(12) United States Patent
Mourtada et al.

(10) Patent No.: US 7,556,596 B2
(45) Date of Patent: Jul. 7, 2009

(54) ADAPTIVE INTRACAVITARY BRACHYTHERAPY APPLICATOR

(75) Inventors: Firas Mourtada, Pearland, TX (US); John Horton, Houston, TX (US); Patricia Eifel, Bellaire, TX (US); Anuja Jhingran, Houston, TX (US); Ira Spool, Brookline, MA (US)

(73) Assignee: Board of Regents The University of Texas System, Austin, TX (US)

( * ) Notice: Subject to any disclaimer, the term of this patent is extended or adjusted under 35 U.S.C. 154(b) by 0 days.

(21) Appl. No.: 11/185,318

(22) Filed: Jul. 20, 2005

(65) Prior Publication Data
US 2006/0235260 A1 Oct. 19, 2006

Related U.S. Application Data

(60) Provisional application No. 60/589,369, filed on Jul. 20, 2004.

(51) Int. Cl.
*A61M 36/00* (2006.01)
*A61M 36/10* (2006.01)
(52) U.S. Cl. .............................. 600/3; 600/6
(58) Field of Classification Search .............. 600/1–8; 128/898, 897; 250/505.1–519.1
See application file for complete search history.

(56) References Cited

U.S. PATENT DOCUMENTS 4,292,960 A * 10/1981 Paglione ....................... 600/2

| | | | |
|---|---|---|---|
| 5,012,357 A | 4/1991 | Schoeppel et al. | |
| 5,213,561 A * | 5/1993 | Weinstein et al. | 600/7 |
| 5,562,594 A | 10/1996 | Weeks | |
| 5,800,333 A * | 9/1998 | Liprie | 600/3 |
| 6,283,911 B1 | 9/2001 | Keren | |
| 6,312,375 B1 | 11/2001 | Montebello et al. | |
| 6,416,492 B1 * | 7/2002 | Nielson | 604/22 |
| 6,540,655 B1 | 4/2003 | Chin et al. | |

FOREIGN PATENT DOCUMENTS

| | | |
|---|---|---|
| DE | 4413490 C1 | 4/1994 |
| EP | 0 972 541 A | 1/2000 |
| WO | WO 01/43826 A | 6/2001 |
| WO | WO 2006/014701 A2 | 2/2006 |
| WO | PCT/US2005/25686 | 12/2006 |

OTHER PUBLICATIONS

Williamson JF.; Dose calculations about shielded gynecological colpostats. Int J Radiat Oncol Biol Phys 1990; 19 (1):167-78.
Lerma FA, Williamson JF.; Accurate localization of intracavitary brachytherapy applicators from 3D CT imaging studies. Med Phys 2002; 29 (3):325-33.

(Continued)

*Primary Examiner*—Samuel G Gilbert
(74) *Attorney, Agent, or Firm*—Vinson & Elkins L.L.P.

(57) ABSTRACT

The invention is a novel adaptive CT-compatible brachytherapy applicator with remotely-controlled radial and longitudinal motion radioactive source lumen shields that can be manipulated by the radiation oncologist to optimize the dose distribution to the target and normal tissue structures for brachytherapy procedures.

41 Claims, 7 Drawing Sheets

OTHER PUBLICATIONS

Mohan R, Ding IY, Martel MK et al.; Measurements of radiation dose distributions for shielded cervical applicators. Int J Radiat Oncol Biol Phys 1985a; 11 (4):861-8.

Mohan R, Ding IY, Toraskar J et al.; Computation of radiation dose distributions for shielded cervical applicators. Int J Radiat Oncol Biol Phys 1985b; 11 (4):823-30.

Weeks KJ. Monte Carlo; Dose calculations for a new ovoid shield system for carcinoma of the uterine cervix. Med Phys 1998; 25 (12):2288-92.

Weeks KJ, Montana GS.; Three-dimensional applicator system for carcinoma of the uterine cervix. Int J Radiat Oncol Biol Phys 1997; 37 (2):455-63.

International Search Report and Written Opinion of the International Searching Authority, International Application No. PCT/US2005/025686, Jul. 16, 2008.

Examination Report, European Patent Application 05778946.3, Dec. 12, 2008.

Supplemental Partial European Search Report, European Application No. 05778946.3, based on PCT/US2005/025686, Nov. 23, 2007.

* cited by examiner

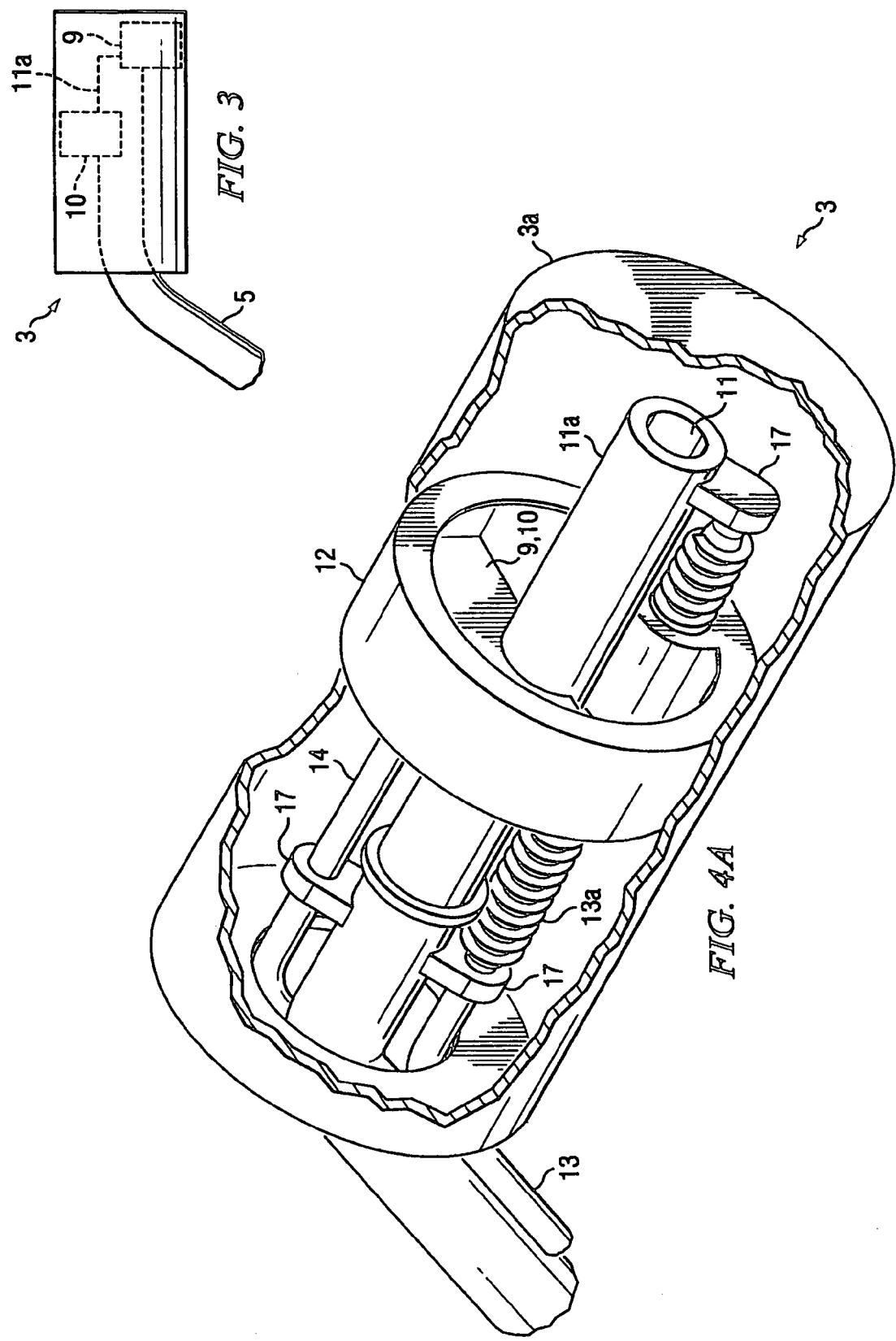

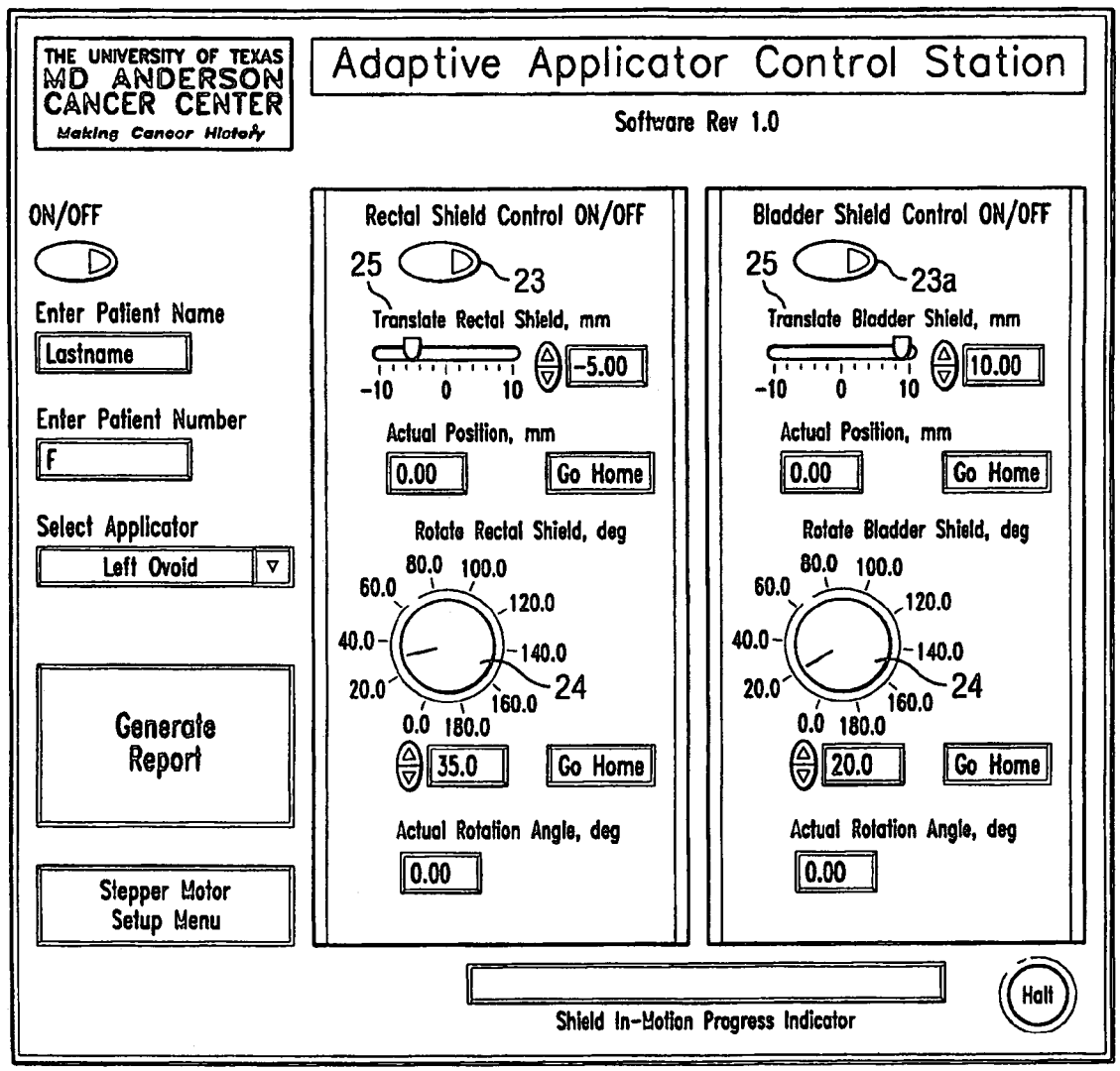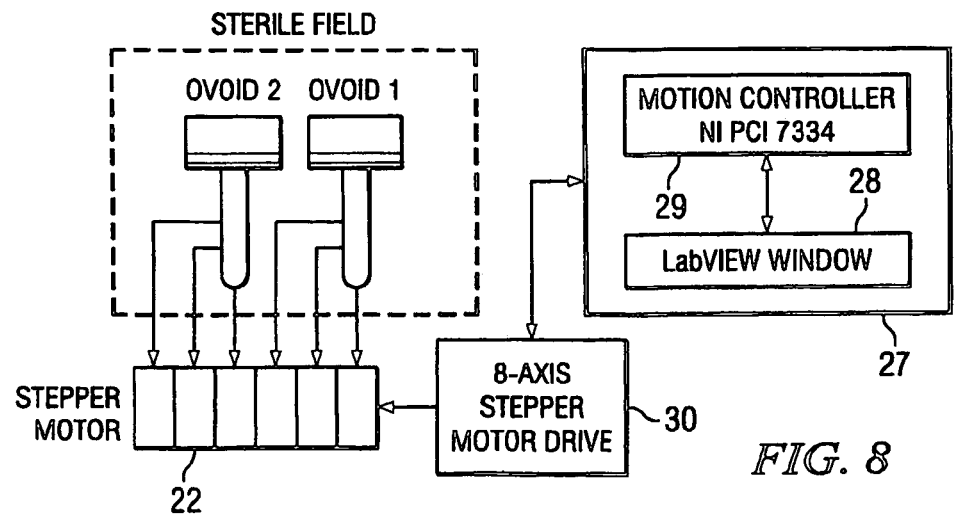
FIG. 8

ADAPTIVE INTRACAVITARY BRACHYTHERAPY APPLICATOR

REFERENCE TO RELATED APPLICATION

This application claims priority to U.S. Provisional application No. 60/589,369, filed Jul. 20, 2004.

BACKGROUND OF THE INVENTION

1. Field of the Invention

The invention of the present disclosure provides a novel adaptive image acquisition-compatible intracavitary brachytherapy (ICBT) applicator with remotely-controlled colpostat shields which may be manipulated to minimize computed-tomography image artifacts or to optimize the dose distribution to the target and normal tissue structures for cancer brachytherapy procedures.

2. Description of Related Art

More than 12,000 new cases of cervical cancer are expected to be diagnosed in the United States in 2003 (American Cancer Society, Cancer Facts and Figures 2003). ICBT is an integral part of the treatment regimen for cervical cancer. It is also used in the treatment of other gynecological malignancies, such as vaginal and endometrial cancer. Combined, these cancers account for about 56,000 new cases in the U.S. each year (American Cancer Society, Cancer Facts and Figures 2003) of which about 20% or 11,200 cases would be treated with ICBT procedures. In addition, worldwide, each year more than 600,000 women develop some form of gynecological cancer, according to the World Health Organization.

Traditionally, many cancers of the cervix are treated with radiation therapy. Between 1996 and 2000, about 84% of these treatments in the U.S. were with low dose rate (LDR) $^{137}$Cs sources, with the remainder using high dose rate (HDR) $^{192}$Ir (Eifel P, et al. Patterns of Radiotherapy Practice for Patients with Carcinoma of the Cervix (1996-1999): A Patterns-of-Care Study. In proceedings of the 45th Annual ASTRO Meeting; 2003). One manner of delivering such radiation is through an ICBT procedure. In an ICBT procedure, radioactive sources are manually or automatically loaded into applicators placed inside the uterine canal during an operative procedure via a procedure termed afterloading. ICBT may, alternatively or additionally, be administered preoperatively or postoperatively and may be paired with external beam radiotherapy, chemotherapy, or both. The targeted cancerous cells or tissue are typically irradiated through the use of a brachytherapy applicator. Current applicators contain left and right ovoids or colpostats and are made of stainless steel. Several varieties of these applicators also have special fixed tungsten shields designed to reduce complications due to inadvertent irradiation of the rectum, bladder or other surrounding tissue. The current practice for positioning of the shield alignment with the bladder and rectum depends on the patient's anatomy and physician's skill.

Additionally, the size, shape, thickness and positioning of these shields may have a substantial effect on the dose of radiation received by normal tissues proximal to the targeted site, particularly the rectum in the case of cervical cancer, and complication rates have been shown to be directly dependent on the dose received by these organs. The clinical treatment planning systems currently used, however, typically are unable to accurately account for the effects of shields resulting in errors of 30% or more in the predicted dose to critical organs (Mohan R, et al. Int J Radiat Oncol Biol Phys 1985a; 11 (4):861-8.; Mohan R, et al. Int J Radiat Oncol Biol Phys 1985b; 11 (4):823-30; Weeks K J, Med Phys 1998; 25 (12): 2288-92; Williamson J F, Int J Radiat Oncol Biol Phys 1990; 19 (1): 167-78). Other studies have shown that dose perturbations resulting from inter-source shielding and applicators are also clinically significant and should be modeled. Fragoso, et al. found that errors as large as 20% could result from not explicitly modeling the steel ovoid applicators and source spacers in LDR treatments (Fragoso M, et al. In Proceedings of the 2003 AAPM Annual Meeting; 2003). Gifford, et al. concluded that explicit modeling of the tandem applicator was also important. Intra-source and inter-source attenuation and the presence of a tip screw were found to have significant effects on the local dose field (Gifford K, et al. In Proceedings of the 2003 AAPM Annual Meeting; 2003).

An integral component in determining the dose distribution to be received by the targeted and non-targeted areas is the positioning of any radiation shielding within the ovoid. ICBT dose distribution planning often involves the use of three dimensional visualization of the targeted areas and surrounding anatomical structures to determine the appropriate position of the implanted applicator in order to maximize a dose distribution of the radiation over the targeted areas. Techniques such as computed-tomography (CT), magnetic resonance (MR), or positron emission tomography (PET) have been employed in the past to generate a three dimensional treatment plan for ICBT procedures. Such techniques are limited by the fact that the shields used in ICBT applicators can interfere with these various methods of planning by distorting images of the implant localization and causing streak artifacts, making a determination of the optimal position of the applicator within the body cavity very difficult to determine.

U.S. Pat. No. 5,562,594 discloses a CT-compatible applicator design (the "Weeks" applicator) that permits CT 3D dosimetry (Weeks K J and Montana G S, Int J Radiat Oncol Biol Phys 1997; 37 (2):455-63). The Weeks ovoid has tungsten-shielded source carriers which are after-loaded post CT image acquisition. The external shape of the Fletcher-Suit-Declos (FSD) minicolpostat tandem and ovoids system appears to have been the basis for the shape of the Weeks applicator. However, the fixed Fletcher-like shields have been removed and replaced with tungsten shields which are manually loaded in conjunction with the $^{137}$Cs sources.

The Weeks applicator has been used to develop a technique for improved CT based applicator localization (Lerma FA and Williamson J F, Med Phys 2002; 29 (3):325-33). This study demonstrated that it was possible to support 3D dose planning involving detailed 3D Monte Carlo dose calculations, modeling source positions, shielding and inter-applicator shielding accurately. Nevertheless, the Weeks applicator has several disadvantages. For example, the Weeks applicator is not adaptable to remote afterloading (loading the radioactive source into the applicator post-insertion and positioning within the body cavity) thereby increasing the radiation exposure from LDR brachytherapy; and it cannot be used at all for HDR or pulsed dose rate (PDR) applications. In addition, in order to accommodate the afterloading shields, the arms connected to the ovoids are much more bulky than those of a standard FSD applicator. The increased size of the arms makes it more difficult to insert the vaginal packing needed to distance the bladder and rectum from the radiation sources. This added bulk also has a potentially negative impact on the comfort of the patient undergoing treatment.

Another available commercial option is the "Standard CT/MR Applicator" based on a Royal Marsden design from Nucletron Corporation. It is designed with special composite tubing to eliminate distortion on CT or MR images. This applicator is available in different lengths and ovoid diameters to optimize the dose distribution and reduce the mucosal dose. This applicator was not designed for use with any shielding however, and thus its use results in exposure of the rectum and bladder or other surrounding tissue to unnecessarily high doses of radiation which may lead to clinical complications.

Therefore, a need exists for a brachytherapy applicator that is amenable to radiation source afterloading but still capable of being manipulated to allow for enhanced image acquisition with minimal artifact generation.

SUMMARY OF THE INVENTION

The present disclosure provides a novel adaptive brachytherapy applicator that is image acquisition-compatible and includes one or more remotely-controlled radially (rotation) and linearly (translation) movable shield(s). This new applicator may be used for LDR, PDR, and/or HDR brachytherapy. Use of certain embodiments of the present invention is expected to improve on the current brachytherapy clinical outcome, in particular by reducing the complications rate. In such embodiments, the ability to alter the position of the shielding during an image acquisition, such as a CT scan, can reduce the imaging artifacts thereby increasing the precision with which important anatomical structures can be delineated. In alternative embodiments the ICBT applicator has, one or more movable shield(s) that can provide an increased degree of freedom thereby allowing an iterative image-guided treatment planning system to optimize or adapt the dose distribution based on a patient-applicator geometrical relationship. In such embodiments, the physician or user can maximize the dose delivered to the target tissue (such as a cervical carcinoma) while concomitantly decreasing the exposure of surrounding tissues (such as in the case of cervical cancer, rectum wall and bladder). In embodiments containing one or more shield(s), the shield(s) motion criteria of the present invention (translation and rotation) will allow treatment to be based on patient/applicator relative relationship as derived from an image modality. The coupling of this technology with a fast (within minutes) dose engine capable of accurately calculating the dose perturbation around a shield(s) can further optimize the use of this invention.

Certain embodiments of the present invention provide a brachytherapy applicator that includes a radioactive source lumen, at least one shield associated with the radiation source lumen, and a mechanical mechanism connected to the shield(s) which is capable of controlling the movement of the shield(s) in at least one direction with respect to the radioactive source lumen.

In other embodiments, the brachytherapy applicator of the present invention includes: a pivot joint; a tandem having a radioactive source lumen; wherein the tandem is connected to the pivot joint through a tandem arm; at least one ovoid having a radioactive source lumen, wherein the at least one ovoid is connected to the pivot joint through an ovoid arm; and at least one shield associated with the at least one ovoid, wherein the at least one shield is remotely-movable. In some of these embodiments, the brachytherapy applicator further includes: a shield track containing the at least one shield, wherein the shield includes a gear interaction region and a counter-treaded member; a rotational shaft having an associated gear which interacts with the gear interaction region of the shield; and a linear shaft having a treaded portion which interacts with the counter-threaded member of the shield track.

In certain embodiments of the brachytherapy applicators of the present invention, the radioactive source lumen is afterloaded with a radioactive source. In embodiments containing ovoids, the radioactive source may be afterloaded through the ovoid arm. In certain other embodiments, the brachytherapy applicators of the present invention, further includes a cap which fits over the source lumen. Some of these applicators also include registration markers that are connected to the source lumen or are present in or on a cap.

In certain alternate embodiments, the at least one shield may be internal to an outer casing enveloping the radioactive source lumen and in some of these embodiments, the shield(s) is composed of tungsten or a tungsten alloy. In alternate embodiments the movement of the shields may be in a linear or rotary fashion. In some of these embodiments, a rotational movement is controlled through a rotational shaft, while a linear motion is controlled through a linear or longitudinal shaft. These shafts may furthermore be composed of nickel-titanium in certain embodiments.

Certain embodiments of the present invention may also include a manual mechanism for applying a rotational force to the rotational shaft or the longitudinal shaft. Alternate embodiments, however, may include a control station controlling the rotational force applied to the rotational shaft or the longitudinal shaft. Furthermore, in some these embodiments, the movement of the shield(s) of the brachytherapy applicator may be remotely controlled through a telemetry signal. In still other embodiments, the position of the shield(s) may be confirmed through a feedback mechanism to confirm, such as optioelectronics.

The present invention also provides methods for treating neoplastic disorders. Certain of these methods include providing a brachytherapy applicator, inserting the brachytherapy applicator into a body cavity, then altering the position of a shield of the brachytherapy applicator after insertion into the body cavity, followed by irradiating neoplastic tissue. Alternate embodiments of these methods also include altering the position of a shield during the image-acquisition phase of the treatment to alter the quality of image artifacts caused by the presence of the applicator. Still other embodiments include altering the position of a shield after a radioactive source has been loaded into the brachytherapy applicator. In some of these embodiments, the position of a shield is altered to change the radiation dose distribution.

BRIEF DESCRIPTION OF THE FIGURES

This invention may be best understood by reference to the following description taken in conjunction with the accompanying drawings, in which like reference numbers identify like elements, and in which:

FIG. 3 is a schematic of one ovoid of a brachytherapy applicator;

FIG. 4A is a schematic of the internal mechanisms of one ovoid of a brachytherapy applicator with an adaptable shield;

FIG. 8 depicts a PC-based control unit for a brachytherapy applicator.

DETAILED DESCRIPTION OF THE INVENTION

Figure 1:
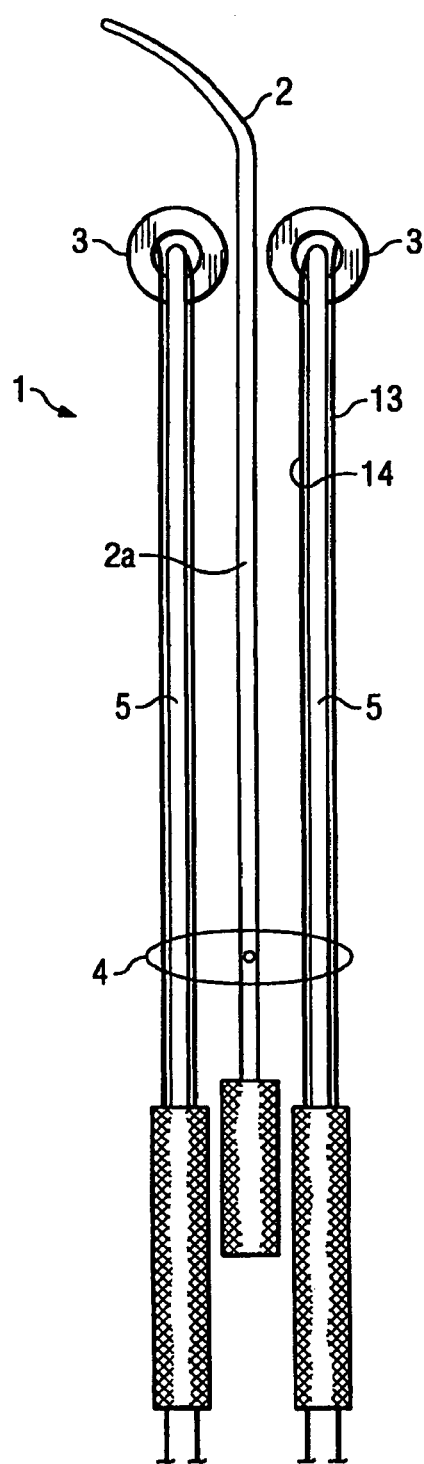
FIG. 1 depicts the basic structure of a brachytherapy applicator.

The present disclosure provides a novel adaptive brachytherapy applicator that is image acquisition-compatible and includes one or more remotely-controlled radially (rotation) and linearly (translation) movable shield(s) within an ovoid (or colpostats), a tandem, or other structure containing a radioactive source lumen. This novel applicator may be used for LDR, PDR, and/or HDR brachytherapy. Use of certain embodiments of the present invention is expected to improve on the current ICBT clinical outcome, in particular by reducing the complications rate.

The ability to alter the position of any shielding during an image acquisition, such as a CT scan, can reduce the imaging artifacts thereby increasing the precision with which important anatomical structures can be delineated. Improvement in target delineation accuracy can allow tailoring of the minimum target dose and the prescription isodose surface shape. In addition, a movable shield(s) can provide an increased degree of freedom thereby allowing an iterative image-guided treatment planning system to optimize or adapt the radiation dose distribution based on a patient-applicator geometrical relationship, hence maximizing the dose delivered to the targeted diseased area, while concomitantly decreasing dose received by tissue protected by the shielding. For example, in treating a cervical carcinoma, the carcinoma dosage could be maximized while the shielding would decrease the rectum wall and bladder radiation doses. In certain embodiments, the shields motion criteria of the present invention can allow treatment to be based on the patient/applicator relative relationship as derived from an image modality.

In other embodiments, the coupling of this technology with a fast (within minutes) dose engine capable of accurately calculating the dose perturbation around a shield(s) can optimize the use of this invention. Fast Monte Carlo or discrete ordinates methods, can also be used in such a capacity.

The introduction of remotely-movable shielding into a brachytherapy device as provided by the present disclosure is adaptable to most any type of brachytherapy device. For example, gynecological, thoracic, head and neck, gastro-intestinal, and breast cancers may be treated with brachytherapy applicators of the present invention. Certain embodiments of the brachytherapy device of the present invention include a radioactive source lumen, which is capable of holding a radioactive source, and shielding that is utilized to reduce or obscure radiation emanating from the source lumen in certain directions. These embodiments, furthermore, include a mechanism for directing the positioning of the shield with respect to the source lumen after the applicator has been inserted into a body cavity. The shielding of these applicators may be internal to the source lumen or may be external to the source lumen (for example, mounted along an ovoid shaft in an FSD-like brachytherapy applicator). The shielding need only be positionable between the radioactive source and the tissue area to be protected from the radiation. Some of these embodiments may contain more than one shield.

In certain embodiments, the positioning of the shield with respect to the radioactive source or source lumen can be manipulated through a mechanical mechanism such as a high torque strength wire or ribbon. In such embodiments, the wire or ribbon may extend from the applicator to a position outside of the patient's body. In certain embodiments, the wire or ribbon maybe inside an outer tubing forming a wire/ribbon-sheath type shaft. The wire or ribbon may have a rotational force applied to it to provide a rotational control over the shield's location. For example, a gear mechanism can be coupled to the shield to provide rotational control. Alternatively, the wire or ribbon can be connected to a threaded member such that the application of a rotational force to the wire will cause the linear movement of a counter-threaded member attached to the shield. Therefore, the shielding in certain embodiments may be positionally controlled in a radial or linear (or both) manner. In certain embodiments, brachytherapy device also includes a locking mechanism to insure shield immobility at the desired location/orientation. While in still other embodiments, a closed loop feedback readout (passive or active), using for example optioelectronics (including fiber optics, LEDs, photodiodes, or the like), is implemented to provide the user with assurance of shield location. Some embodiments also include a default "home" position of the shield(s) that is defined based on the current FSD ovoid concept.

Alternative embodiments of the present invention may utilize a remote control mechanism associated with the shielding and which does not extend proximally outside of the patients body. In such embodiments, the position of the shielding may be controlled via an external signal, which activates or deactivates a mechanical mechanism associated with the applicator to manipulate the position of the shield(s). Such signals may include, but are not limited to, radio waves, infrared waves, and sound waves or other telemetry methods.

FIG. 1 depicts the structure of one embodiment of a FDS-like ICBT applicator of the present invention. This embodiment of the applicator includes a tandem 2 connected to a pivot joint 4 through a tandem arm 2a and a pair of colpostats/ovoids 3 which are connected to the pivot joint 4 through a pair of ovoid arms 5. In certain embodiments the pivot joint 4 serves only to connect the tandem arm 2a to the ovoid arm 5, while in certain other embodiments, the pivot joint 4 functions not only as a connection point but also enables alterations of the angle between the tandem arm 2a and the ovoid arm 5. The tandem 2 and the ovoids 3 are designed to hold a radioactive source(s) during irradiation of a patient. In certain embodiments, the tandem arm 2a and/or ovoid arms 5 may be adapted to allow the radioactive source(s) to be loaded through them into the tandem and ovoids, respectively. This can be done after the applicator has been positioned within the body cavity in a process termed afterloading.

Figure 2:
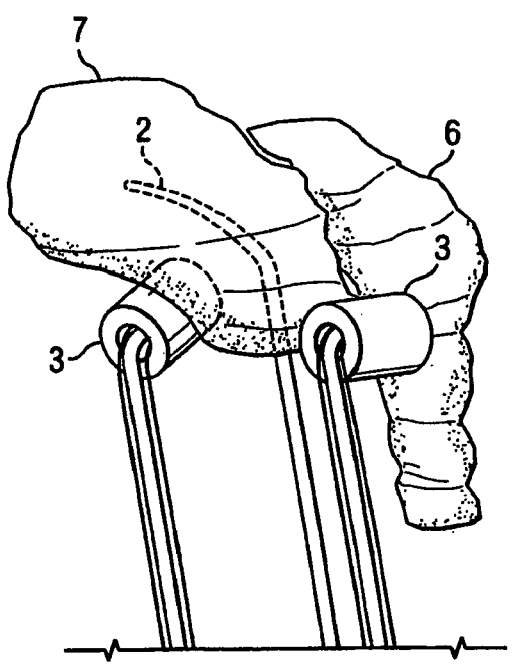
FIG. 2 depicts the position of a brachytherapy applicator within the patient.

FIG. 2 depicts the positioning of an FSD-like ICBT applicator of the present invention during treatment of a patient having cervical cancer. The tandem 2 is inserted into the uterus 7 while the ovoids 3 are positioned in the vagina proximal to the external os of the cervix.

During an intracavitary brachytherapy treatment an FSD-like embodiment of the present invention (as shown in FIG. 1) may be used. Radioactive sources can be placed within the tandem 2 and the ovoids 3 to provide a pear-shaped dose distribution that just surrounds a target volume, with its long axis along the tandem axis. In certain embodiments of the present invention, the radioactive source(s) can be after-loaded into the applicator. In some of these embodiments, the radioactive source is inserted in the ovoids 3 through the ovoid arms 5 and the radioactive source is loaded into the tandem 2 through the tandem arm 2a. Prior to the loading of the radioactive source during such procedures, the applicator is often positioned in the body cavity and images, such as orthogonal x-ray films, CT scans, MR scans, and/or PET scans, are acquired to confirm its location. These images can also be used to determine and verify that the applicator has been positioned optimally with respect to anatomical location and the dosage of radiation that will be delivered to the targeted area.

FIG. 3 provides a schematic of an ovoid 3 containing a rectal shield 9, a bladder shield 10 and a radioactive source lumen 11. These shields may be composed of any material that will attenuate, partially or wholly, the radiation from the source that travels into it. A typical example of such a material is tungsten, tungsten alloys, titanium, platinum, or any suitable high atomic number element. Furthermore, the shield(s) may be of varying size, shape and thickness. A person of skill in the art will chose the size, shape and thickness based on the tissue being treated, the patient, the radiation source and other relevant factors. In some embodiments of the current invention, the shield(s) may be interchangeable such that an attending oncologist may choose a shield of a specific size, shape and thickness that will provide the optimal shielding in relation to the patient's anatomy, delineated target volume, delineated critical structures, the radioactive source utilized, or other factors.

During the treatment planning phase, the proper positioning for maximal shielding of non target tissue, such as the bladder and the rectum in the case of cervical cancer, is calculated. In the applicators of the prior art, the shields would then typically be affixed in a permanent position prior to inserting the device into the body cavity or affixed to a delivery vehicle of some type and delivered to the applicator along with the radioactive source (such as in the Weeks applicator). The present invention, however, discloses applicators that include mechanisms for adjusting the shield position after the applicator, including the shielding, has been inserted into the body cavity.

FIG. 4A depicts a schematic of one embodiment of an ovoid of the present invention that includes a positionally adjustable shield. This shield may be positioned to protect non-target tissues such as the rectum or the bladder, preferably the rectum in the case of cervical cancer. This embodiment of the present invention includes an ovoid cap 3a which surrounds the radioactive source lumen 11. The ovoid cap 3a provides a housing for a shield track 12 which is associated with a shield 9. The shield track 12 and shield 9 are movable in a longitudinal or linear fashion with respect to the central axes of the ovoid 3 itself, while the shield 9 is also moveable in a radial fashion with respect to the central axis of the ovoid. The shield track 12 can be functionally engaged by a threaded shaft 13, a rotational shaft 14 or both. The threaded shaft 13 can include a threaded section 13a at or near its end and is capable of moving the shielding track 12 linearly up and down (distal to proximal) the ovoid 3. The rotational shaft 14 is capable of rotating the shield 9 radially with respect to the longitudinal center of the ovoid 3.

In certain embodiments the rotational shaft or threaded shaft are composed of a wire or ribbon of a shape memory alloy such as nickel titanium or the like, although other material possessing a high torsional strength can also be used. The rotational shaft or threaded shaft can alternatively be made of braided metal filaments or braided or solid filaments of high strength synthetic fibers.

Figure 4B:
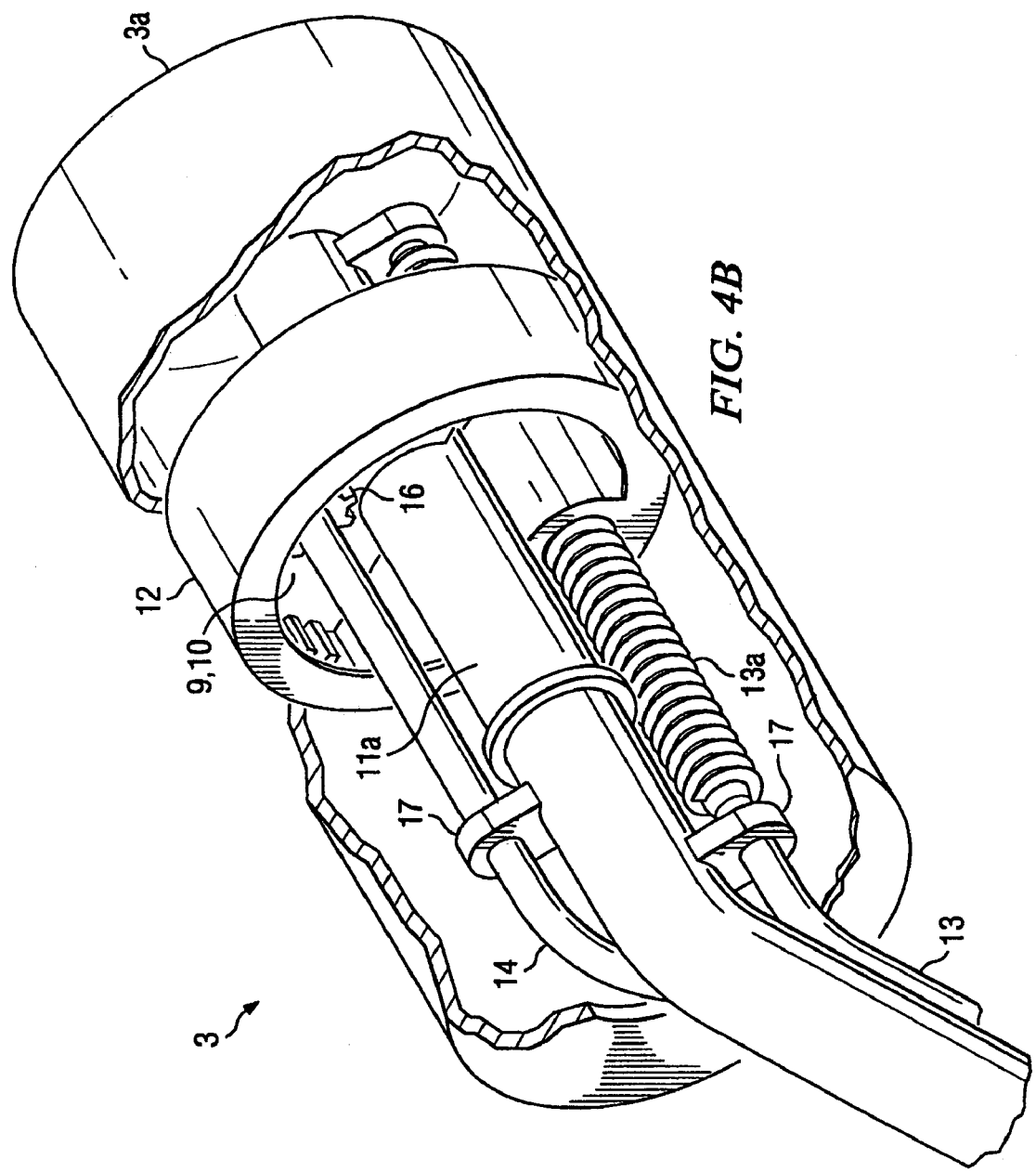
FIG. 4B is a schematic of the internal mechanisms of one ovoid of a brachytherapy applicator with an adaptable shield from a proximal view.
Figure 5:
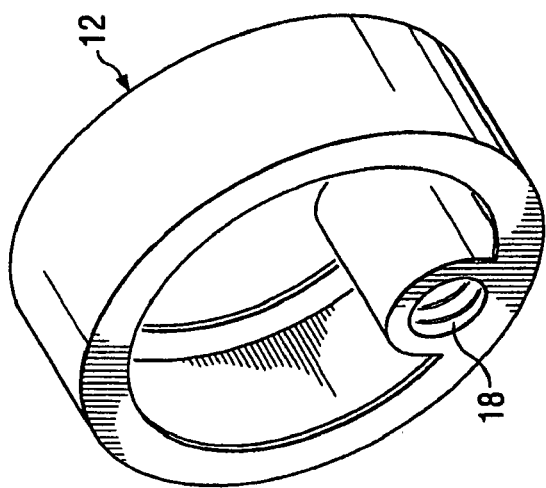
FIG. 5 shows a schematic of a shield track.

In certain embodiments, the position of a shield 9 can be adjusted manually through a mechanical interaction of the threaded and/or rotational shafts 13/14 (as shown in FIG. 4A) with the shield track 12 or shield 9/10 respectively. As depicted in FIG. 4B, a gear 16 associated with the rotational shaft 14 at or near its distal end can engage the shield 9/10 in such a manner that a rotation force (torque) applied to the rotational shaft 14 would cause the gear 16 to move the shield 9/10 radially. In a similar fashion, rotational force (torque) applied to the threaded shaft 13 may engage a counter-threaded housing 18 (as depicted in FIG. 5) associated with the shield track 12 causing the shield track 12 to move longitudinally with respect to the ovoid shaft 11a. In certain embodiments the shield track may contain mechanical stops to restrict the degrees of rotation through which the shield track 12 and shield 9/10 may travel.

Figure 4C:
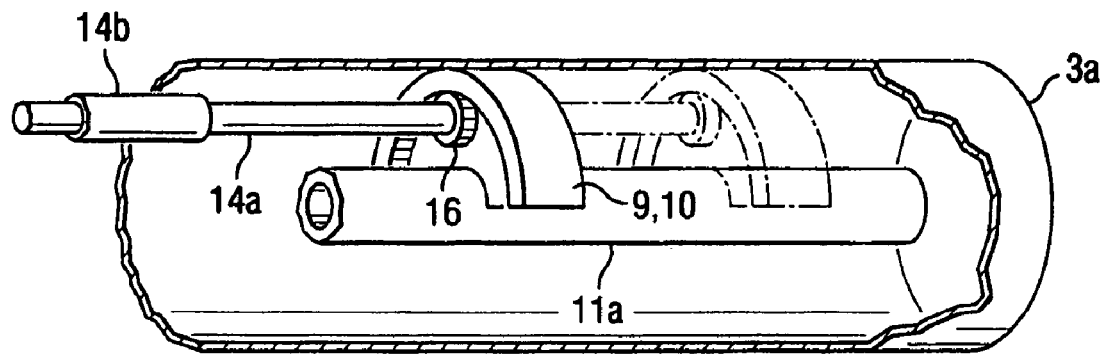
FIG. 4C depicts the association of a rotary shaft with a sleeve/shaft.
Figure 4D:
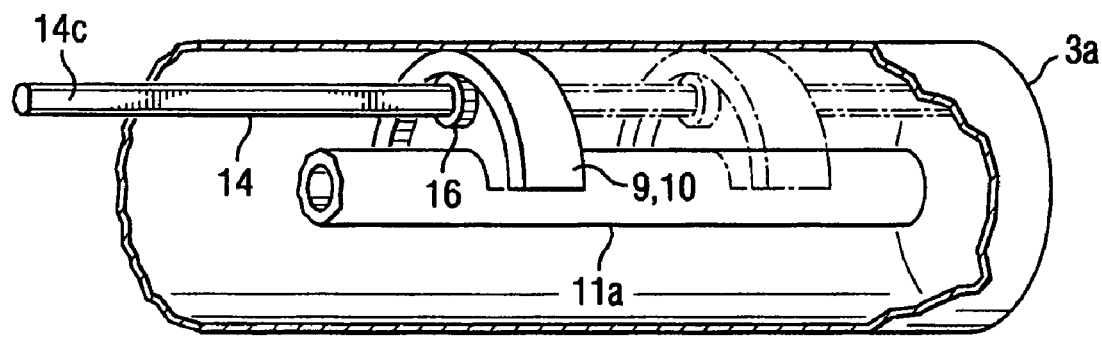
FIG. 4D depicts the association of a rotary shaft with a flat side.
Figure 4E:
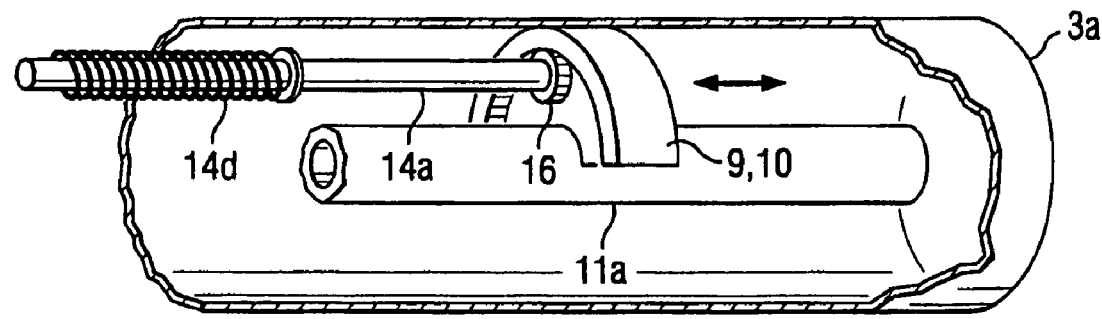
FIG. 4E depicts the association of a rotary shaft with a spring.

When the shield 9 is moved linearly (proximal or distal) the "rotary shaft" 14a may slide inside of its tube 14b (similar to the way a wire may be pulled out of its insulation) in such a fashion as to maintain contact between the gear 16 and the shield 9 (as shown in FIG. 4C). In alternate embodiments (as shown in 4D), a rotary shaft having a flat side 14c that extends through the gear 16 toward the distal end of the ovoid cap 3a may be used. In these embodiments the gear 16 may slide linearly along rotary shaft 14 along with the shield 9/10 and shield track 12 to maintain its interaction with the shield 9/10. In still other embodiments, a spring-loaded portion of the rotary shaft 14d may be used to maintain the interaction of the gear 16 with the shield 9/10 as the shield track is moved linearly along the ovoid 3 (as shown in FIG. 4E).

The shield track 12, the gear 16, or the threaded section of the threaded shaft 13 (the "motion parts") may be made of any suitable material. In certain embodiments, the material used to make these motion parts will be based on mechanical strength (tensile and shear), tissue radiation-characteristics equivalency, fatigue and thermal properties to allow for multiple sterilization cycles. In some embodiments, these motion parts are made of Polysulfone or Polycarbonate or other tissue-equivalent material that will contribute to a minimal perturbation to the dose distribution when compared to the transitional applicators.

Figure 6A:
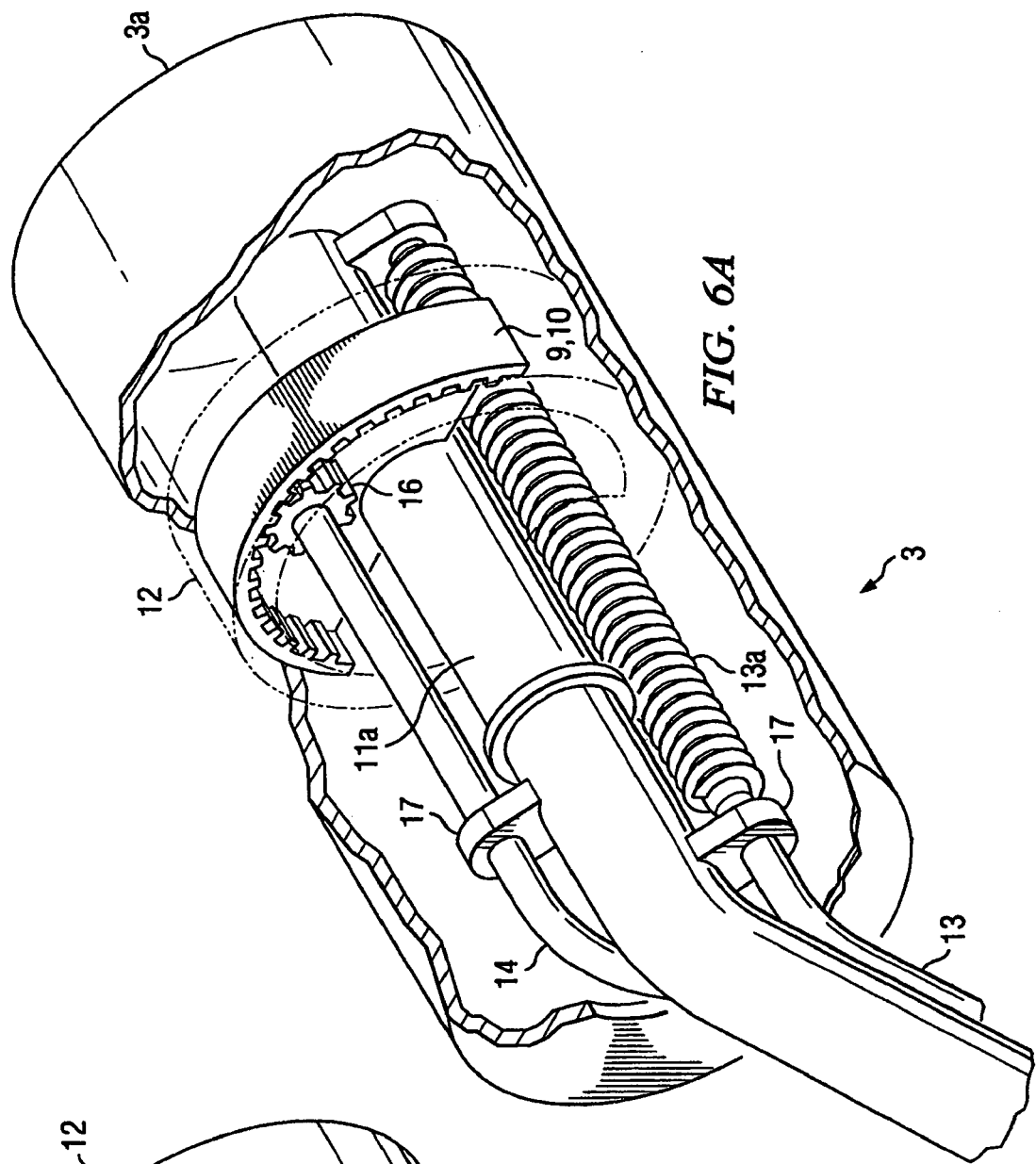
FIG. 6A displays the position of a shield with respect to the internal mechanisms of an ovoid.
Figure 6B:
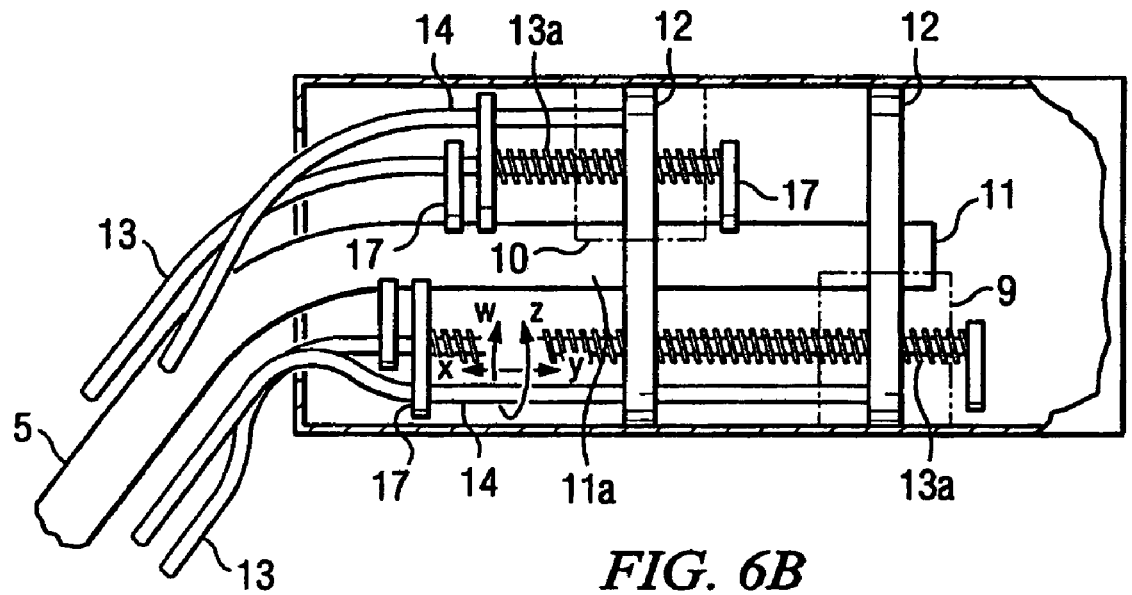
FIG. 6B is a schematic showing the positioning of shields with respect to the internal mechanisms of an ovoid.

FIG. 6A provides an internal view of the ovoid 3 with a shield 9/10 with the shield track 12 as shown in FIG. 4B, removed for clarity. In certain embodiments, the rotational shaft 14 and the threaded shaft 13 can run through and be supported by ovoid supports 17 which also engage the casing of the source lumen 11a. In alternate embodiments of the present invention, such as depicted in FIG. 6B, the ovoid can house a thread shaft 13 and a rotational shaft 14 for more than one shield 9/10. In such embodiments there can be a rectal shield 9, a bladder shield 10 or both, each having its own independent shield track 12. In certain such embodiments, the shield track 12 associated with the rectal shield 9 may be in a position which is closer to the distal end of the ovoid 3 as compared to the bladder shield 10. Such embodiments would be able to independently position, both radially and linearly, the rectal shield 9 and the bladder shield 10.

Alternate embodiments, may include more than one shield wherein one or more of the shields may be affixed with respect its position relative to the radioactive source and not be engaged by the positional machinery within the ovoid 3. For example, in one embodiment, a bladder shield can be affixed to the ovoid shaft 11a, while the rectal shield 9 is positionally moveable by the rotational shaft 14 through the rotational gear 16 and the threaded shaft 13 through the counter-threaded housing 18 through its association with a shield track 12. Still other embodiments may allow for the opposite configurations in which a bladder shield 10 is associated with a shield track 12, while a rectal shield would be affixed.

In certain embodiments, the ovoid 3 may have a removable ovoid cap 3a that can be detached from the ovoid to expose the shield and other motion parts to allow for a quality assurance visual inspection or to perform corrective maintenance. In still other embodiments, the ovoid cap 3a of the present invention itself may be adaptable to increase the overall size of the ovoid 3 to match the anatomy of a given patient. In certain other embodiments, the adaptive applicator of the present invention will have an overall profile of the ovoid handle (proximal tubing) similar to current Nucletron Fletcher-Williamson HDR applicator set (~5 mm outer tubing diameter) to provide for seamless integration in the clinic. While in still other embodiments, the adaptive applicator profile can be slightly larger to accommodate channels for the threaded and rotational shafts 13/14 (~7 mm outer tubing diameter).

In certain embodiments, the angle of an ovoid's linear axis with respect to the ovoid arm is adjustable. In some of these embodiments, the angle is adjustable between 15° and 45°. In still other embodiments a wire/ribbon may interact with a gear driven mechanism that allows for remotely controlled alterations of the shape or size of the shield.

Figure 7:
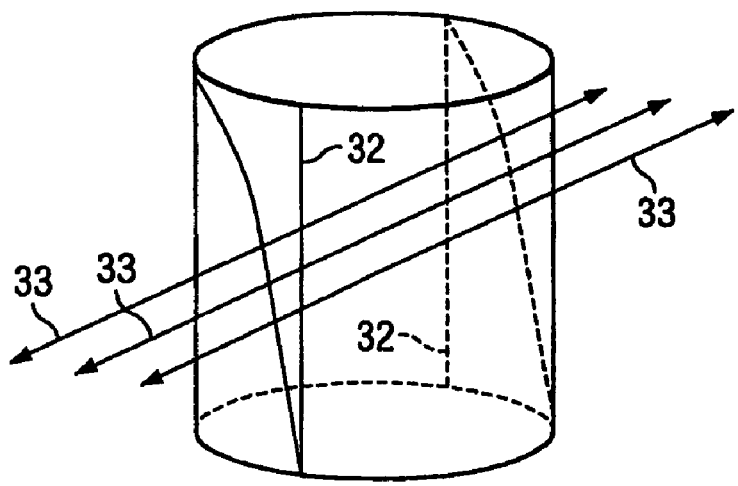
FIG. 7 depicts the position of registration wires in an ovoid cap.

Furthermore, certain embodiments of the present invention may include registration markers. These registration markers provide markers during image-acquisition which enable positional locations of the shields to be determined or verified with respect to the patient's anatomy. These registration markers may be composed of any radiopaque substance and, in some embodiments, may be in the form of a wire. The registration markers may be included in or on various portions of the applicators of present invention, including the source lumen, tandem or ovoid. FIG. 7 depicts one embodiment of an ovoid 3 having registration wires 32 parallel and diagonal to, the ovoid. In such an embodiment, the registration wires 32 may be positioned at an angle to the plane in which image slices 33 will be taken. Other embodiments of the present invention may have a variety of other configurations of the registration markers. In certain embodiments, the registration markers may be associated with the default location of the shield(s). In these embodiments, the images acquired will have registration marks identifying, directly or indirectly, the default location of the shield(s), thereby, enabling a more precise determination of the shield movements necessary to achieve optional positioning of the shields.

In certain embodiments the registration markers can be embedded in the casing for the source lumen or ovoid shaft 11a. In still others the registration markers may be on or in caps which are positionable on the ovoid 3 itself.

In certain embodiments, Monte Carlo or discrete-ordinate dosimetric simulation of the adaptive applicator of the present invention may be used to determine the final selection of the range of linear/angular motion for the rectum shield, the bladder shield, or both. Furthermore, the ability of the present invention to internally adjust the location of a shield both longitudinally and radially allows for the movement of the shield during CT image acquisition, or any other type of image acquisition, thereby allowing the attendant to decrease the artifacts produced by the shielding in a brachytherapy applicator and provide a more precise and enhanced images for use in the treatment planning. For example, the applicator can be inserted into a body cavity and images then acquired with the shield(s) moved to a position most proximal along the ovoid axis. A single slice CT scanner could then acquire a first image set before reaching the location of the moved shield. The scanner acquisition can then be briefly interrupted to move the shield to most distal location before resuming acquisition of the rest of the CT slices. An initial scout image of the CT simulator can be performed to select the interruption position between the two image sets. In addition to allowing for the capture of enhanced images, certain embodiments of the present invention allow for inverse-treatment planning of the treatment regime. For example, the radioactive source may be loaded into the applicator with the shield in a predetermined position and then subsequently have the shield positions or shield position adjusted during the radiation exposure in order to manipulate the dose distribution in a more precise fashion.

In certain embodiments, the applicator of the present invention also includes a manual mechanism for applying a rotational force on the threaded shaft 13 or the rotational shaft 14. These manual mechanisms may include simple mechanical attachments to the shaft, such a turn screw connect to the shaft. In still other embodiments, the rotation of the rotational or threaded shaft may be controlled using dial indicators for simplicity. In such embodiments, each mechanical dial may have a scale to show the location and orientation of the shield being adjusted. The dials may, furthermore, be designed for convenient surgical access.

Alternate embodiments of the present invention may use a computer 27 as a control station. In certain such embodiments, the hardware components may include a laptop computer with LabVIEW software 28 and PCI motion-controller card 29 from National Instruments, Austin, Tex. (www.ni.com), a motion control drive unit 30 having multiple axes. The position of the shield or shields may be controlled through a control station 27 as depicted in FIG. 8. This control station may control the rotational position of a given shield through a rotational control 24 and the linearly position through a linear control 25. In certain embodiments, the rectal shield and the bladder shield may have independent control stations (23 and 23a). The control stations, in certain embodiments, may control the activity of a motor 22 which would provide the rotational force on the rotational shaft or the threaded shaft.

In certain embodiments, the control station or the applicator itself may have an automatic homing position (default) that mimics the FSD applicator (for LDR) or the Flecher-Williamson applicator (for HDR/PDR) shield locations.

The control station in certain embodiments may be used to position the shielding in the appropriate location prior to loading of the radioactive source into the applicator or the radioactive source may be loaded into the applicator with the shield in a predetermined position and then subsequently have the shield positions or shield position adjusted during the radiation exposure in order to manipulate the dose distribution in a more precise fashion to conform the prescribed pear-shaped isodose surface to the delineated target volume. Radiobiological-corrected dose volume-histogram treatment planning algorithms can also be used to further optimize the shield location along the course of the treatment.

What is claimed is:

1. A brachytherapy applicator comprising:
   a radioactive source lumen;
   at least one shield associated with the radiation source lumen; and
   a mechanical mechanism connected to the at least one shield which is capable of controlling the radial and linear movement of the at least one shield with respect to the associated radioactive source lumen.

2. The brachytherapy applicator of claim 1, wherein a radioactive source is afterloaded into the radioactive source lumen.

3. The brachytherapy applicator of claim 1, wherein the at least one shield is inside the source lumen.

4. The brachytherapy applicator of claim 1, wherein the mechanical mechanism is remotely controlled through a telemetry signal.

5. The brachytherapy applicator of claim 1, further comprising a feedback mechanism to confirm the position of the at least one shield.

6. The brachytherapy applicator of claim 5, wherein the feedback mechanism comprises optioelectronics.

7. The brachytherapy applicator of claim 1, further comprising at least one registration marker connected to the source lumen.

8. The brachytherapy applicator of claim 1, further comprising a cap which fits over the source lumen.

9. The brachytherapy applicator of claim 8, further comprising at least one registration marker in the cap.

10. The brachytherapy applicator of claim 8, further comprising at least one registration marker on the cap.

11. The brachytherapy applicator of claim 1, wherein the radioactive source lumen is adapted for having a radioactive source afterloaded.

12. A brachytherapy applicator comprising:
a pivot joint;
a tandem having a radioactive source lumen, wherein the tandem is connected to the pivot joint through a tandem arm;
at least one ovoid having a radioactive source lumen, wherein the at least one ovoid is connected to the pivot joint through an ovoid arm; and
at least one shield associated with the at least one ovoid, wherein the radial and linear movement of the at least one shield is remotely-movable with respect to the associated radioactive source lumen.

13. The brachytherapy applicator of claim 12, wherein the radioactive source lumen of the at least one ovoid is afterloaded with a radioactive source.

14. The brachytherapy applicator of claim 13, wherein the radioactive source lumen is adapted for having a radioactive source afterloaded through the ovoid arm.

15. The brachytherapy applicator of claim 13, wherein the radioactive source is afterloaded into the radioactive source lumen through the ovoid arm.

16. The brachytherapy applicator of claim 12, further comprising:
a shield track containing the at least one shield, wherein the shield includes a gear interaction region and a counter-threaded member;
a rotational shaft having an associated gear which interacts with the gear interaction region of the shield; and
a linear shaft having a treaded portion which interacts with the counter-threaded member of the shield track.

17. The brachytherapy applicator of claim 16, wherein the radioactive source lumen of the at least one ovoid is capable of being afterloaded with a radioactive source.

18. The brachytherapy applicator of claim 16, wherein the radioactive source is afterloaded into the radioactive source lumen through the ovoid arm.

19. The brachytherapy applicator of claim 16, wherein the at least one ovoid further comprises an outer casing and the at least one shield is internal to the outer casing of the at least one ovoid.

20. The brachytherapy applicator of claim 16, wherein the at least one shield is composed of tungsten or a tungsten alloy.

21. The brachytherapy applicator of claim 16, wherein the rotational shaft or the longitudinal shaft is composed of nickel-titanium.

22. The brachytherapy applicator of claim 16, further comprising a manual mechanism for applying a rotational force to the rotational shaft or the longitudinal shaft.

23. The brachytherapy applicator of claim 16, further comprising a control station controlling the rotational force applied to the rotational shaft or the longitudinal shaft.

24. The brachytherapy applicator of claim 16, wherein the radioactive source lumen of the at least one ovoid is adapted for having a radioactive source afterloaded.

25. The brachytherapy applicator of claim 16, wherein the radioactive source lumen is adapted for having a radioactive source afterloaded through the ovoid arm.

26. The brachytherapy applicator of claim 12, wherein the at least one ovoid further comprises an outer casing and the at least one shield is internal to the outer casing of the at least one ovoid.

27. The brachytherapy applicator of claim 12, wherein the radioactive source lumen of the at least one ovoid is adapted for having a radioactive source afterloaded.

28. A method of treating neoplastic disorders comprising:
providing the brachytherapy applicator of claim 1;
inserting the brachytherapy applicator of claim 1 into a body cavity;
altering the position of the at least one shield of the brachytherapy applicator of claim 1 after insertion into the body cavity; and
irradiating neoplastic tissue.

29. The method of claim 28, further comprising altering the position of the at least one shield during an image-acquisition phase of the treatment to alter the quality of image artifacts caused by the presence of the applicator.

30. The method of claim 28, further comprising altering the position of the at least one shield after a radioactive source has been loaded in the brachytherapy applicator of claim 1.

31. The method of claim 28, further comprising changing the position of the at least one shield for the purpose of altering the radioactive dose distribution.

32. The method of claim 31, wherein the radioactive dose distribution is altered to decrease the radioactive dose applied to normal tissue.

33. The method of claim 32, wherein the normal tissue is cervical tissue, rectal tissue or bladder tissue.

34. A method of treating neoplastic disorders comprising:
providing the brachytherapy applicator of claim 12;
inserting the brachytherapy applicator of claim 12 into a body cavity;
altering the position of the at least one shield of the brachytherapy applicator of claim 12 after insertion into the body cavity; and
irradiating neoplastic tissue.

35. The method of claim 34, further comprising altering the position of the at least one shield during the image-acquisition phase of the treatment to alter the quality of image artifacts caused by the presence of the brachytherapy applicator.

36. The method of claim 34, further comprising altering the position of the at least one shield after a radioactive source has been loaded in the brachytherapy applicator of claim 12.

37. The method of claim 34, further comprising changing the position of the at least one shield for the purpose of altering the radioactive dose distribution.

38. The method of claim 37, wherein the radioactive dose distribution is altered to decrease the radioactive dose applied to normal tissue.

39. The method of claim 38, wherein the normal tissue is cervical tissue, rectal tissue or bladder tissue.

40. A brachytherapy applicator comprising:

a radioactive source lumen, wherein the radioactive source lumen is adapted for having a radioactive source afterloaded;

at least one shield associated with the radiation source lumen; and a mechanical mechanism connected to the at least one shield which is capable of controlling the radial movement of the at least one shield with respect to the radioactive source lumen, wherein the mechanical mechanism is remotely controlled through a telemetry signal.

41. A brachytherapy applicator comprising:

a pivot joint;

a tandem having a radioactive source lumen, wherein the tandem is connected to the pivot joint through a tandem arm;

at least one ovoid having a radioactive source lumen, wherein the at least one ovoid is connected to the pivot joint through an ovoid arm, and wherein the radioactive source lumen of the at least one ovoid is adapted for having a radioactive source afterloaded;

at least one shield associated with the at least one ovoid, wherein the at least one shield is remotely-movable;

a shield track containing the at least one shield, wherein the shield includes a gear interaction region and a counter-threaded member;

a rotational shaft having an associated gear which interacts with the gear interaction region of the shield;

a linear shaft having a threaded portion which interacts with the counter-threaded member of the shield track;

a control station controlling the rotational force applied to the rotational shaft or to the longitudinal shaft, wherein the movement of the at least one shield is remotely controlled through at least one telemetry signal; and a feedback mechanism to confirm the positioning of the at least one shield.

* * * * *

UNITED STATES PATENT AND TRADEMARK OFFICE
CERTIFICATE OF CORRECTION

PATENT NO.        : 7,556,596 B2
APPLICATION NO. : 11/185318
DATED             : July 7, 2009
INVENTOR(S)       : Firas Mourtada et al.

It is certified that error appears in the above-identified patent and that said Letters Patent is hereby corrected as shown below:

Column 11, line 51, for the claim reference numeral 16, please delete "treaded" and insert --threaded--.

Column 14, line 13, for the claim reference numeral 41, please delete "longitudinal" and insert --linear--.

Signed and Sealed this

Twenty-fifth Day of August, 2009

David J. Kappos
*Director of the United States Patent and Trademark Office*